United States Patent
Yuan et al.

(10) Patent No.: US 8,618,104 B2
(45) Date of Patent: *Dec. 31, 2013

(54) SALTS OF METHYL (R)-7-[3-AMINO-4-(2,4,5-TRIFLUORO-PHENYL)-BUTYRYL]-3-TRIFLUOROMETHYL-5,6,7,8-TETRAHYDRO-IMIDAZO[1,5-A]PYRAZINE-1-CARBOXYLATE

(75) Inventors: Kaihon Yuan, Lianyungang Jiangsu (CN); Shuqin Ma, Lianyungang Jiangsu (CN); Lin Zhu, Lianyungang Jiangsu (CN); Huawen Liu, Lianyungang Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 73 days.

This patent is subject to a terminal disclaimer.

(21) Appl. No.: 13/322,142

(22) PCT Filed: Apr. 29, 2010

(86) PCT No.: PCT/CN2010/072319
§ 371 (c)(1),
(2), (4) Date: Jan. 11, 2012

(87) PCT Pub. No.: WO2010/135944
PCT Pub. Date: Dec. 2, 2010

(65) Prior Publication Data
US 2012/0122875 A1    May 17, 2012

(30) Foreign Application Priority Data
May 27, 2009   (CN) .......................... 2009 1 0145237

(51) Int. Cl.
*A61K 31/4985* (2006.01)
*A61P 3/10* (2006.01)

(52) U.S. Cl.
USPC ...................................................... 514/249

(58) Field of Classification Search
None
See application file for complete search history.

(56) References Cited

U.S. PATENT DOCUMENTS

| 5,462,928 | A | 10/1995 | Bachovchin et al. | |
| 5,543,396 | A | 8/1996 | Powers et al. | |
| 8,207,161 | B2* | 6/2012 | Tang et al. | 514/249 |
| 2009/0105265 | A1* | 4/2009 | Kamali et al. | 514/249 |

FOREIGN PATENT DOCUMENTS

| CN | 101468988 A | | 7/2009 | |
| WO | WO-95/15309 A1 | | 6/1995 | |
| WO | WO 03/004498 | * | 1/2003 | .......... C07D 487/04 |
| WO | WO-03004498 A1 | | 1/2003 | |
| WO | WO-03/082817 A2 | | 10/2003 | |
| WO | WO 2004/032836 | * | 4/2004 | |
| WO | WO-2004032836 A2 | | 4/2004 | |
| WO | WO 2004/058266 | * | 7/2004 | .......... A61K 31/497 |
| WO | WO-2004085661 A2 | | 10/2004 | |
| WO | WO-2008157751 A2 | | 12/2008 | |
| WO | WO 2009/082881 | * | 7/2009 | ................ A61P 3/04 |

OTHER PUBLICATIONS

'Salify Definition' at www.thefreedictionary.com/salify (retrieved from the interenet on May 19, 2013).*
Amori et al. JAMA 2007; 298(2)194-206.*
White et al. Clinical Diabetes 26(2), 2008, 53-57.*
International Search Report dated Aug. 5, 2010, for corresponding International Application No. PCT/CN2010/072319.
Augustyns, et al., "Inhibitors of proline-specific dipeptidyl peptidases: DPP IV inhibitors as a novel approach for the treatment of Type 2 diabetes", Expert Opin. Ther. Patents, 15(10): 1387-1407 (2005).
Demuth, et al., "Type 2 diabetes—Therapy with dipeptidyl peptidase IV inhibitors", Biochimica et Biophysica Acta, 1751: 33-44 (2005).

* cited by examiner

*Primary Examiner* — Dennis Heyer
(74) *Attorney, Agent, or Firm* — Mintz Levin Cohn Ferris Glovsky and Popeo, P.C.

(57) ABSTRACT

The pharmaceutically acceptable salts of methyl (R)-7-[3-amino-4-(2,4,5-trifluoro-phenyl)-butyryl]-3-trifluoromethyl-5,6,7,8-tetrahydro-imidazo[1,5-a]pyrazine-1-carboxylate, their preparation methods and their use for preparing anti-diabetic medicaments are disclosed.

17 Claims, No Drawings

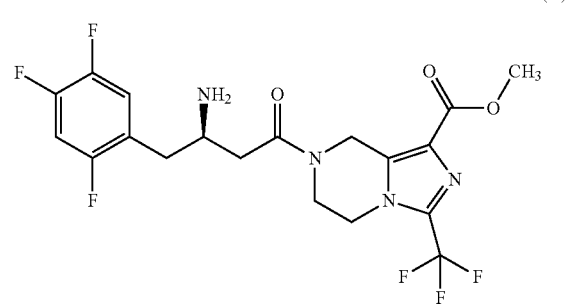

(A)

SALTS OF METHYL (R)-7-[3-AMINO-4-(2,4,5-TRIFLUORO-PHENYL)-BUTYRYL]-3-TRIFLUOROMETHYL-5,6,7,8-TETRAHYDRO-IMIDAZO[1,5-A]PYRAZINE-1-CARBOXYLATE

CROSS-REFERENCE TO RELATED APPLICATIONS

This application is a U.S. national phase application under 37 U.S.C. §371 of Patent Cooperation Treaty Application No. PCT/CN2010/072319 filed on Apr. 29, 2010, which claims the priority benefit of Chinese Patent Application No. 200910145237.8 filed on May 27, 2009. The disclosure of each application listed in this paragraph is incorporated by reference herein in its entirety.

FIELD OF THE INVENTION

The present invention relates to pharmaceutically acceptable salts of methyl (R)-7-[3-amino-4-(2,4,5-trifluoro-phenyl)-butyryl]-3-trifluoromethyl-5,6,7,8-tetrahydro-imidazo[1,5-a]pyrazine-1-carboxylate and the preparation methods thereof, as well as their use for the preparation of antidiabetic medicaments.

BACKGROUND OF THE INVENTION

Relevant datas from WHO showed morbidity rate, disability rate, death rate of diabetes mellitus and overall health level of diabetes mellitus patients have already ranked the third place in non-infectious diseases, diabetes, together with tumors and cardiovascular diseases were the three main diseases which threats human health. Diabetes mellitus is usually classified into type 1 and type 2, there are more than 240 million diabetes patients, and 90% of them are suffering from type 2 diabetes, which also has a 1% growth rate every year, so, type 2 diabetes will be the main new growth point of diabetes drug market. The incidence of diabetes in China is about 5%, the number of patients of which ranks second place in the world just behind India. There are many antidiabetic drugs on the market, insulin injection, metformin, rosiglitazone, pioglitazone are representations of them. However, there is no drug alone can keep the HbAlc level of type 2 diabetes patients within the aimed range in a long term. Even though used in combination, the effect of the drugs will go down year by year after 3-4 years. Adverse reaction is one of the problems of many hypoglycemic drugs, wherein the fatal hypoglycemia is most worried by clinicians; secondly, many oral hypoglycemic drugs, such as sulfonylureas, α-glycosidase inhibitors and thiazolidinediones may all induce weight gain to patients, some of the drugs may also induce cardiovascular diseases.

Therefore, developing new type hypoglycemic drugs with brand new mechanism of action, higher safety and effectiveness is an important task that should be completed quickly for the scientists.

In the process of constantly finding new methods endocrine hormones were found to play an important role in the pathology and physiology of type 2 diabetes. Dipeptidyl peptidase-IV (DPP-IV) is an important enzyme related to diabetes, inhibiting the action of which to treat type 2 diabetes is a new method with good prospect. DPP-IV inhibitors can indirectly stimulate the secretion of insulin, the action of which is generated by inhibit DPP-IV to stabilize endocrine hormones such as incretin hormones, glucagons-like-peptide-1 (GLP-1) and glucose-dependent insulinotropic peptide (GIP).

GLP-1 is a production expressed by glucagon protogene after eating, and mainly secreted by intestinal mucosa L-cell, and it can stimulate the secretion of insulin by pancreatic β-cells, which plays a significant role in the stability of blood sugar. Experiments prove that GLP-1 has physiological functions as following: acting on pancreatic β-cells in a glucose-dependent manner, facilitating the transcription of insulin genes, increasing the biosynthesis and secretion of insulin, stimulating the proliferation and differentiation of β-cells, inhibiting the apoptosis of β-cells to increasing the number of pancreatic β-cells; inhibiting the secretion of glucagon; inhibiting the appetite and food intake; retarding the emptying of gastric contents, etc., all of these functions are helpful to reduce blood sugar after food intake and to keep blood sugar within constant level. In addition, it won't cause the danger of severe hypoglycemia. GLP-1 well controlled the blood sugar of type 2 diabetes animal models and patients by multiple mechanisms. However, GLP-1 may lose biological activity through quick degradation by DPP-IV, and the half life of it is shorter than 2 minutes, which utterly limits the clinical use of GLP-1. It was found in researches that DPP-IV inhibitors can totally protect endogenous and even extraneous GLP-1 from inactivation by DPP-IV, improve activated GLP-1level, and reduce the antagonistic effect of GLP-1 metabolites. Moreover, DPP-IV inhibitors can also delay the incidence of diabetes through stimulating the regeneration of pancreatic β-cells and the improving the glucose tolerance and insulin sensitivity.

Dipeptidyl peptidase-IV (DPP-IV) inhibitors represent a novel class of agents that are being developed for the treatment or improvement in glycemic control in patients with Type 2 diabetes. For reviews on the application of DPP-IV inhibitors for the treatment of Type 2 diabetes, reference is made to the following publications: (1) H.-U. Demuth. et al. "Type 2 diabetes-Theraphy with dipeptidyl peptidase IV inhibitors", Biochim. Biophvs. Acta. 1751:33-44 (2005) and (2) K. Augustyns. et al. "Inhibitors of proline-specific dipeptidyl peptidases: DPP4 inhibitors as a novel approach for the treatment of Type 2 diabetes", Expert Opin. Ther. Patants, 15:1387-1407 (2005).

At present, some DPP-IV inhibitors have been disclosed (U.S. Pat. No. 5,462,928, U.S. Pat. No. 5,543,396, WO9515309, WO2003004498, WO2003082817, WO2004032836, WO2004085661), including MK-0431 as an DPP-IV inhibitor made by Merck which showed good inhibition activity and selectivity, and which has been on the market by 2006.

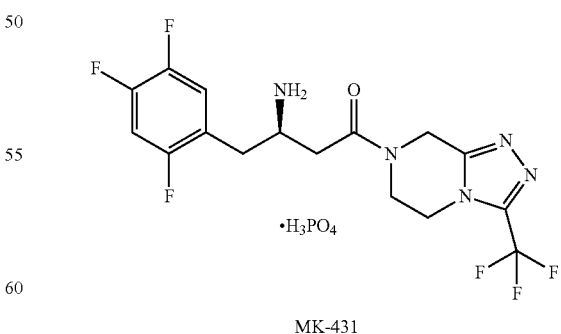

MK-431

(R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester of the following formula is compound A, the code of which is SP2086.

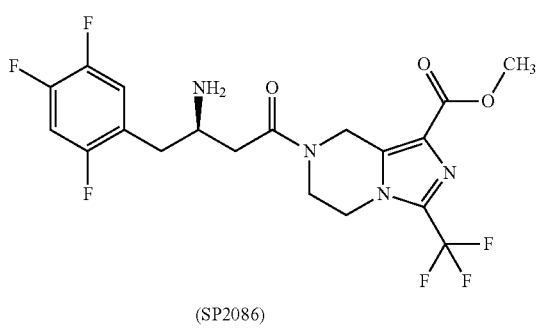

Compound A (SP2086)

SUMMARY OF THE INVENTION

The present invention relates to pharmaceutically acceptable salts of compound A and the preparation methods thereof, preferably relates to the advantages of phosphate or hydrochloride of compound A compared to other salts in stability, antidiabetic activity and pharmacokinetics.

One aspect of the present invention relates to pharmaceutically acceptable salts of (R)-7-[3-amino-4-(2,4,5-trifluoro-phenyl)-butyryl]-3-trifluoro-methyl-5,6,7,8-tetrahydro-imidazo[1,5-a]pyrazine-1-carboxylic acid methyl ester, wherein said salts were conventional inorganic salts or organic salts in the art, further, said inorganic salt is selected from the group consisting of hydrochloride salt, hydrobromide salt, sulphate salt, nitrate salt or phosphate salt, preferably hydrochloride salt, sulphate salt or phosphate salt, most preferably hydrochloride salt or phosphate salt; and said organic salt is selected from the group consisting of mesylate salt, maleate salt, tartrate salt, succinate salt, acetate salt, trifluoroacetate salt, fumarate salt, citrate salt, benzene sulfonate salt, benzoate salt, naphthalenesulfonate sulfonate salt, lactate salt or malate salt, preferably malate salt, mesylate salt or maleate salt. Particularly preferred pharmaceutically acceptable salts are hydrochloride salt and phosphate salt which are more advantageous in stability, antidiabetic activity and pharmacokinetics compared to other salts.

Another aspect of the present invention relates to the preparation methods of the pharmaceutically acceptable salts of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester, which could be prepared according to the conventional salification methods in the art.

The present invention further relates to a pharmaceutical composition comprising therapeutically effective amount of pharmaceutically acceptable salt of (R)-7-[3-amino-4-(2,4,5-trifluoro-phenyl)-butyryl]-3-trifluoro-methyl-5,6,7,8-tetrahydro-imidazo[1,5-a]pyrazine-1-carboxylic acid methyl ester and pharmaceutically acceptable carriers.

The present invention also relates to the use of pharmaceutically acceptable salts of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester and the pharmaceutical compositions thereof in the preparation of antidiabetic drugs.

The hydrochloride salt and phosphate salt of compound A are superior to compound A itself and the other salts of it in stability, antidiabetic activity and pharmacokinetics.

Synthesis Method of the Critical Material
SM2086-15 in the Present Invention

The synthesis method of (R)-7-[3-t-butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid methyl ester refers to the preparation method described in the example 1 of PCT/CN2008/001936, the disclosure of which is herein incorporated by reference.

DETAILED DESCRIPTION OF THE INVENTION

Example 1

Preparation of Hydrochloride of Compound A (SP2086-HCL)

(R)-7-[3-t-butoxycarbonylamino-4-(2,4,5-trifluoro-phenyl)-butyryl]-3-trifluoromethyl-5,6,7,8-tetrahydro-imidazo[1,5-a]pyrazine-1-carboxylic acid methyl ester (SM2086-15) (1.35 kg, 2.40 mol), HCL-ethyl acetate (greater than 2M) (12.3 kg) were added into a 100 L reaction kettle and stirred to dissolved. The mixture was reacted for more than 2 hours at normal temperature. Detected with TLC to reaction completely before evaporated and pumped to dryness with oil pump to give 1.15~1.20 kg of white to light yellow solid product with $[\alpha]_D^{20}$ −28.0~−33.0° (C=1, methanol), yield 96.0~100%. The product was hydrochloride of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester (SP2086-HCL). (TLC detection: silica gel $GF_{254}$ plate; developing reagent: chloroform:methanol:ammonia=40:1:0.1; raw material 15: Rf=0.80, product 1: Rf=0.50; ultraviolet visualization).

Example 2

Preparation of Phosphate of Compound A (SP2086-$H_3PO_4$)

SP2086-HCL (1.20 kg, 2.40 mol) was added into 100 L reaction kettle, and dissolved in dichloromethane (15.2 kg), then washed with saturated sodium bicarbonate solution (5.8 kg). The aqueous layer was extracted once with dichloromethane (6.0 kg). The organic layers were combined and washed once with water (5 kg), dried with anhydrous sodium sulphate. The mixture was filtrated and concentrated to dryness under reduced pressure at 40° C. to give 1.12 kg of oil. The oil was stirred and dissolved with 30 times amount of isopropanol (26.0 kg). A solution of 85% phosphoric acid (305.2 g, 2.65 mol) in isopropanol (1.22 kg) was added immidiately after the oil completely dissolved. The solid was separated out, filtered after stirring for 2 hours and washed with cold isopropanol. The wet product was dried under reduced pressure at 40° C. to give 1.16~1.24 kg of white to light yellow solid with a yield of 86.0-92.0% (the wet product could be directly suspended in isopropanol without drying).

Example 3

Preparation of Mesylate of Compound A

Hydrochloride of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester (SP2086-HCL) (1.20 kg, 2.40 mol) was added into 100 L reaction kettle, and dissolved in dichloromethane (15.2 kg), then washed with saturated sodium bicarbonate solution (5.8 kg). The aqueous layer was extracted once with dichloromethane (6.0 kg). The organic layers were combined and washed once with water (5 kg), dried with anhydrous sodium sulphate. The mixture was filtrated and concentrated to dryness under reduced pressure at 40° C. to give 1.12 kg of oil. The oil was stirred and dissolved with 30 times amount of isopropanol (26.0 kg). A solution of methanesulfonic acid (254.7 g, 2.65 mol) in isopropanol (1.22 kg) was added immidiately after the oil completely dissolved. The solid was separated out, filtered after stirring for 2 hours, and washed with cold isopropanol. The wet product was dried under reduced pressure at 40° C. to give 1.08~1.21 g of white to light yellow solid with a yield of 79.5%~89.3%.

Example 4

Preparation of Sulfate of Compound A

Hydrochloride of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester (SP2086-HCL) (1.20 kg, 2.40 mol) was added into 100 L reaction kettle and dissolved in dichloromethane (15.2 kg), then washed with saturated sodium bicarbonate solution (5.8 kg). The aqueous layer was extracted once with dichloromethane (6.0 kg). The organic layers were combined and washed once with water (5 kg), dried with anhydrous sodium sulphate. The mixture was filtrated, concentrated to dryness under reduced pressure at 40° C. to give 1.12 kg of oil. The oil was stirred and dissolved with 30 times amount of isopropanol (26.0 kg). A solution of 98% sulfuric acid (265.0 g, 2.65 mol) in isopropanol (1.22 kg) was added immidiately after the oil completely dissolved. The solid was separated out, filtered after stirring for 2 hours and washed with cold isopropanol. The wet product was dried under reduced pressure at 40° C. to give 1.14-1.25 kg of white to light yellow solid matter with a yield of 85.5-93.0% (the wet product could be directly suspended in isopropanol without drying).

Example 5

Malate of Compound A

Hydrochloride of (R)-7-[3-amino-4-(2,4,5-trifluoro-phenyl)-butyryl]-3-trifluoromethyl-5,6,7,8-tetrahydro-imidazo pyrazine-1-carboxylic acid methyl ester (SP2086-HCL) (1.20 kg, 2.40 mol) was added into 100 L reaction kettle and dissolved in dichloromethane (15.2 kg), then washed with saturated sodium bicarbonate solution (5.8 kg). The aqueous layer was extracted once with dichloromethane (6.0 kg). The organic layers were combined and washed once with water (5 kg), dried anhydrous with sodium sulphate. The mixture was filtrated, concentrated to dryness under reduced pressure at 40° C. to give 1.12 kg of oil. The oil was stirred and dissolved with 30 times amount of isopropanol (26.0 kg). A solution of L-malic acid (355.34 g, 2.65 mol) in isopropanol (1.22 kg) was added immediately after the oil completely dissolved. The solid was separated out, filtered after stirring for 2 hours, and washed with cold isopropanol. The wet product was dried under reduced pressure at 40° C. to give 1.19~1.32 kg of white to light yellow solid matter with a yield of 87.5~92.0% (the wet product could be directly suspended in isopropanol without drying).

Example 6

Maleate of Compound A

Hydrochloride of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester (SP2086-HCL) (1.20 kg, 2.40 mol) was added into 100 L reaction kettle and dissolved in dichloromethane (15.2 kg), then washed with saturated sodium bicarbonate solution (5.8 kg). The aqueous layer was extracted once with dichloromethane (6.0 kg). The organic layers were combined and washed once with water (5 kg), dried with sodium sulphate anhydrous. The mixture was filtrated, concentrated to dryness under reduced pressure at 40° C. to give 1.12 kg of oil. The oil was stirred and dissolved with 30 times amount of isopropanol (26.0 kg). A solution of maleic acid (307.59 g, 2.65 mol) in isopropanol (1.22 kg) was added immediately after the oil completely dissolved. The solid was separated out, filtered after stirring for 2 hours, and washed with cold isopropanol. The wet product was dried under reduced pressure at 40° C. to give 1.19~1.32 kg of white to light yellow solid matter with a yield of 87.5~92.0% (the wet product could be directly suspended in isopropanol without drying).

Example 7

Stability of Compound A and its Salts (1) Content Determination Method

With a Octadecyl silane chemically bonded silica as bulking agent and 0.1% aqueous solution of ammonia-acetonitrile (65:35) as mobile phase, eluted in gradient mode at detection wavelength of 230 nm. Appropriate amount of test sample and reference solution was taken, then water was added to dissolve which to form solutions every 1 ml containing 0.2 mg of them respectively. The test sample solution and reference solution 10 μl was respectively taken and injected into the liquid chromatograph. chromatograph chart was recorded, and calculated by peak area according to the external standard method.

| time (min) | 0.1% aqueous ammonia (%) | acetonitrile (%) |
|---|---|---|
| 0 | 65 | 35 |
| 25 | 45 | 35 |
| 35 | 45 | 35 |

(2) Determination Results

The stability of different types of the pharmaceutically acceptable salts of compound A under different conditions (Raw material purity: 98.6%, use HPLC to determine their contents)

| | name | | | | | | |
|---|---|---|---|---|---|---|---|
| condition | Compound A | Hydrochloride | Mesylate | Sulfate | Shosphate | Malate | Maleate |
| 10 days Light | 95.2% | 98.1% | 97.6% | 97.6% | 98.6% | 95.7% | 94.2% |
| 40° C. 10 days | 95.2% | 98.7% | 96.7% | 96.6% | 98.7% | 96.8% | 94.2% |
| 60° C. 10 days | 95.7% | 98.2% | 96.5% | 97.7% | 98.5% | 96.5% | 96.2% |

-continued

| condition | Compound A | Hydrochloride | Mesylate | Sulfate | Shosphate | Malate | Maleate |
|---|---|---|---|---|---|---|---|
| RH75% Six months 40° C. | 92.2% | 97.7% | 95.4% | 96.2% | 98.3% | 97.2% | 93.8% |
| RH60% nine months 25° C. | 93.3% | 97.5% | 95.6% | 96.7% | 98.6% | 94.9% | 94.6% |

Conclusion: The stability test results showed that hydrochloride and phosphate of Compound A are the most satisfying, especially the stability of its phosphate, and the stability of above-mentioned two salts are better than the compound A itself.

Example 8

The Related Biological Activities Study of the Pharmaceutically Acceptable Salts of Compound A Test Example 1

Compound A, MK-0431 In Vitro Activity and Selectivity Study

Method: Thawed DPP4-Glo. was buffered and balanced to room temperature, and cryopreserved fluorescein test agent was buffered before use. DPP4-Glo. was suspended in substrate and ultrapure water was added, the mixture was mixed slightly to uniformity to provide 1 mM of substrate. The fluorescein test agent was put into amber bottle, and DPP4-Glo. was added. The fluorescein test agent should be dissolved in 1 min. The test compound was dissolved with DMSO to 50 times of the final processing concentration. 2 µL of test compound of 50 times concentration was added into each test tube, and 2 µL of DMSO was added into negative control and blank control. 46 µL of Tris buffer solution was added into each test tube, and 48 µL of Tris buffer was added into blank control. 2 µL of DPP4 enzyme was added into each test tube of negative control and test sample, and the test tubes were shaken and mixed, and then centrifuged. The substances in the test tubes were all transferred to a 96-well plate, and the substrates and DPP4-Glo. were mixed in a proportion of 1:49. The mixture was shaken and mixed adequately. 50 µL of the mixture of DDP4-Glo. and the substrate was added into each 96-well plate well after standing for 30-60 minutes at room temperature, the plate was sealed with film. The substances in the 96 wells were mixed slowly with plate scillator at 300-500 rmp/30 s. After cultivation for 30 minutes to 3 hours at room temperature, the chemiluminescence value was measured with NOVOstar multifunction microplate reader.

TABLE 1

| Tested compounds | DPP4 IC50 (M) | DPP8 IC50 (M) | DPP8 Selectivity ratio (DPP8/DPP4) | DPP9 IC50 (M) | DPP9 Selectivity ratio (DPP9/DPP4) |
|---|---|---|---|---|---|
| Compound A | 0.008 | 26.1 | 3263 | 75.5 | 9438 |
| MK-0431 | 0.019 | 25.8 | 1358 | 92.7 | 4879 |

Results: The inhibition activity on DPP4 of compound A is stronger than the control drug MK-0431, and its selectivity is also higher than MK-0431. Higher value of DPP8/DPPIV and DPP9/DPPIV means better activity.

Test Example 2

The Effects of the 6 Salts of Compound A in Genetic Obese Wistar Rats with Diabetes 14 to 19 week-old male Wistar fat rats were divided into five groups, each to group 5 to 6, and they were respectively administered the 6 salts of compound A (each 10 mg/kg weight/day, p.o.) which were mixed in commercial feed at a ratio of 5 ppm for 14 days. The blood was taken from tail vein, a commercial kits (NC-ROPET, Nippon Chemiphar CO.) was used to measure plasma glucose and hemoglobin A1 by enzymatic is method. The results were expressed as mean value of each group (n=5-6)±standard deviation and analyzed by Dunnett's test which were shown in table 2. A significance level of 1% was used.

TABLE 2

| | Plasma glucose | Hemoglobin |
|---|---|---|
| Control group | 352 ± 32 | 5.9 ± 0.5 |
| Phosphate of compound A | 158 ± 24* | 4.3 ± 0.6* |
| Sulfate of compound A | 327 ± 46 | 5.4 ± 0.6 |
| Hydrochloride of compound A | 165 ± 13* | 4.5 ± 0.5* |
| Maleate of compound A | 294 ± 51* | 5.3 ± 0.3 |
| Malate of compound A | 295 ± 42 | 5.2 ± 0.6 |
| Mesylate of compound A | 287 ± 34 | 5.8 ± 0.4 |

*Compared with the control group, $p < 0.01$

In table 2, hydrochloride and phosphate of Compound A reduce the concentration of blood glucose and hemoglobin obviously, which are stronger than the others. The most preference was phosphate.

Test Example 3

Glucose Tolerance Research of Various Salts of Compound A in the Genetic Obese Wistar Rats with Diabetes 13~14 week-old male fat rats were divided into five groups, each group five. They were respectively administered the 6 salts of compound A (each 30 mg/kg/day, p.o.) for 7 days. After overnight fasting, oral glucose tolerance tests were conducted immidiately (2 g glucose/kg/5 ml, p.o.). Before and 120 and 240 mins after the glucose tolerance test, blood was collected from the tail vein, and plasma glucose was analyzed by enzymatic method (Encore Chemical System;

Baker). Results were expressed as mean value of each group (n=5-6)±standard deviation analyzed by Dunnett's test which were shown in table 3.

TABLE 3

| | Plasma glucose (mg/dl) | | |
|---|---|---|---|
| | 0 min | 120 min | 240 min |
| Control group | 121 ± 8 | 243 ± 60 | 139 ± 20 |
| Phosphate of compound A | 107 ± 3 | 95 ± 10* | 68 ± 5* |
| Sulfate of compound A | 120 ± 12 | 224 ± 62 | 117 ± 21 |
| Hydrochloride of compound A | 109 ± 5 | 116 ± 7* | 106 ± 3* |
| Maleate of compound A | 103 ± 11 | 137 ± 17* | 102 ± 9* |
| Malate of compound A | 110 ± 9 | 114 ± 12* | 95 ± 6* |
| Mesylate of compound A | 108 ± 8 | 115 ± 9* | 92 ± 7* |

*Compared with the control group, $p < 0.01$

Table 3 clearly indicated that hydrochloride and phosphate of compound A significantly inhibited the increase of blood sugar after the glucose tolerance tests, which were stronger than the others. Phosphate of compound A is particularly preferable.

Test Example 4

Absorption Tests in Rats of Different Salts of Compound A

Dosage Regimen:

16 healthy male rats weighing 200~220 g were randomly divided into four groups. 6.0 mg/kg (by base) phosphate salt (A), hydrochloride salt (B), maleate salt (C), methanesulfonate salt (D) of compound A (administration volume was 10 ml/kg, respectively in the form of 0.60 mg/ml (by base) of suspension prepared with 0.5% of CMC—Na) were given by gavage, fasting 12 hours before administration, free drinking. 0.3 ml of vein blood was respectively collected from postocular venous plexus of the rats before and 0.167, 0.333, 0.50, 1.0, 2.0, 3.0, 4.0, 5.0, 6.0, 8.0 and 12 hours after administration, blood was put into heparinized tubes, centrifuged at 3500 rpm for 10 mins. The plasma was separated, preserved for test under −20° C. The blood concentration was tested by HPLC-Tandem Mass Spectrum.

Average pharmacokinetic parameters after 6.0 mg/kg of different salts of compound A were administrated to the rats by gavage.

| Preparation | $t_{1/2}$ (h) | $C_{max}$ (ng/mL) | $T_{max}$ (h) | $AUC_{0-t}$ (ng·h/mL) | $AUC_{0-\infty}$ (ng·h/mL) | MRT (h) | CL/F (mL/min/kg) |
|---|---|---|---|---|---|---|---|
| A | 1.54 | 242 | 0.50 | 409 | 425 | 1.96 | 545 |
| B | 1.07 | 148 | 0.63 | 317 | 319 | 1.86 | 348 |
| C | 0.75 | 231 | 0.50 | 306 | 307 | 1.24 | 326 |
| D | 0.87 | 133 | 0.88 | 274 | 275 | 1.61 | 397 |

Conclusion: Pharmacokinetics profile of the phosphate of compound A was best.

What is claimed is:

1. A composition comprising:
a pharmaceutically acceptable salt of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic methyl ester.

2. The composition according to claim 1, wherein the pharmaceutically acceptable salt comprises an inorganic salt.

3. The composition according to claim 2, wherein the inorganic salt is selected from the group consisting of phosphate salt, hydrochloride salt, sulfate salt, nitrate salt or hydrobromide salt.

4. The composition according to claim 1, wherein the pharmaceutically acceptable salt comprises an organic salt.

5. The composition according to claim 1, wherein the organic salt is selected from the group consisting of mesylate salt, maleate salt, tartrate salt, succinate salt, acetate salt, trifluoroacetate salt, fumarate salt, citrate salt, benzene sulfonate salt, benzoate salt, naphthalenesulfonate salt, lactate salt, and malate salt.

6. A method comprising:
salifying (R)-7-[3-amino-4-(2,4,5-trifluoro-phenyl)-butyryl]-3-trifluoromethyl-5,6,7,8-tetrahydro-imidazo[1,5-a]pyrazine-1-carboxylic methyl ester with a corresponding acid, the salifying producing a pharmaceutically acceptable salt of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic methyl ester.

7. The method according to claim 6, further comprising combining a therapeutically effective amount of the pharmaceutically acceptable salt of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic methyl ester and a pharmaceutically acceptable carrier to prepare a medicament for the treatment of diabetes.

8. The composition according to claim 1, further comprising:
a therapeutically effective amount of the pharmaceutically acceptable salt of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic methyl ester; and
a pharmaceutically acceptable carrier.

9. The method according to claim 6, wherein the pharmaceutically acceptable salt comprises an inorganic salt.

10. The method according to claim 9, wherein the inorganic salt is selected from the group consisting of phosphate salt, hydrochloride salt, sulfate salt, nitrate salt or hydrobromide salt.

11. The method according to claim 6, wherein the pharmaceutically acceptable salt comprises an organic salt.

12. The method according to claim 11, wherein the organic salt is selected from the group consisting of mesylate salt, maleate salt, tartrate salt, succinate salt, acetate salt, trifluoroacetate salt, fumarate salt, citrate salt, benzene sulfonate salt, benzoate salt, naphthalenesulfonate salt, lactate salt, and malate salt.

13. A method for treating Type-2 diabetes, the method comprising:
delivering a therapeutically effective amount of a pharmaceutically acceptable salt of (R)-7-[3-amino-4-(2,4,5-trifluoro-phenyl)-butyryl]-3-trifluoromethyl-5,6,7,8-tetrahydro-imidazo[1,5-a]pyrazine-1-carboxylic acid methyl ester in a pharmaceutically acceptable carrier.

14. The method for treating diabetes according to claim 13, wherein the pharmaceutically acceptable salt comprises an inorganic salt.

15. The method for treating diabetes according to claim 14, wherein the inorganic salt is selected from the group consisting of phosphate salt, hydrochloride salt, sulfate salt, nitrate salt or hydrobromide salt.

16. The method for treating diabetes according to claim 13, wherein the pharmaceutically acceptable salt comprises an organic salt.

17. The method for treating diabetes according to claim 16, wherein the organic salt is selected from the group consisting of mesylate salt, maleate salt, tartrate salt, succinate salt, acetate salt, trifluoroacetate salt, fumarate salt, citrate salt, benzene sulfonate salt, benzoate salt, naphthalenesulfonate salt, lactate salt, and malate salt.

* * * * *